United States Patent [19]

Mager et al.

[11] Patent Number: 5,067,966
[45] Date of Patent: Nov. 26, 1991

[54] 2-AMINO-6-CHLORO-4-NITRO-PHENOL DERIVATIVES, PROCESS TO THEIR PRODUCTION AND HAIR DYES CONTAINING THOSE COMPOUNDS

[75] Inventors: Herbert Mager, Marly; Braun, Hans-Jürgen, Ueberstorf, both of Fed. Rep. of Germany

[73] Assignee: Wella Aktiengesellschaft, Darmstadt, Fed. Rep. of Germany

[21] Appl. No.: 573,177
[22] PCT Filed: Dec. 12, 1989
[86] PCT No.: PCT/EP89/01523
 § 371 Date: Aug. 17, 1990
 § 102(e) Date: Aug. 17, 1990
[87] PCT Pub. No.: WO90/07557
 PCT Pub. Date: Jul. 12, 1990

[30] Foreign Application Priority Data

Dec. 23, 1988 [DE] Fed. Rep. of Germany ....... 3843578

[51] Int. Cl.$^5$ ..................... A61K 7/13; C07C 321/00; C07C 211/00
[52] U.S. Cl. .......................................... 8/405; 8/406; 8/414; 8/416; 564/440; 564/441
[58] Field of Search ................. 8/405, 406, 414, 416, 8/417; 564/440, 441

[56] References Cited

U.S. PATENT DOCUMENTS 2,750,326 6/1956 Eckardt ................. 564/441
4,125,601 11/1978 Bugaut ................. 564/441
4,575,378 3/1986 Seidel et al. ............. 8/414

FOREIGN PATENT DOCUMENTS 1210810 11/1970 United Kingdom .
2104895 3/1983 United Kingdom .

Primary Examiner—Paul Lieberman
Assistant Examiner—William S. Parks
Attorney, Agent, or Firm—Michael J. Striker

[57] ABSTRACT

The improved hair dye compounds are 2-amino-6-chloro-4-nitrophenol derivatives of the general formula (I)

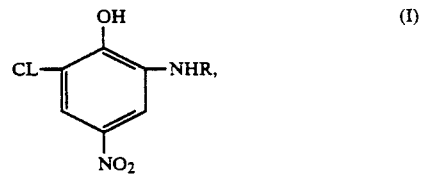

wherein the radical R is a straight-chain or branched alkyl group with 1 to 5 carbon atoms. These hair dye compounds may be made by substitution of an amine group hydrogen of 2-amino-6-chloro-4-nitrophenol to form the amide and subsequent reduction, preferably with sodium borohydride. The hair dye compositions contain a compound of formula (I). The compounds of formula (I) dye the hair an intense red and can be favorably tolerated physiologically.

16 Claims, No Drawings

2-AMINO-6-CHLORO-4-NITRO-PHENOL DERIVATIVES, PROCESS TO THEIR PRODUCTION AND HAIR DYES CONTAINING THOSE COMPOUNDS

BACKGROUND OF THE INVENTION

The subject matter of the invention concerns new 2-amino-6-chloro-4-nitrophenol derivatives, processes for their production and hair dye compositions which contain 2-amino-6-chloro-4-nitrophenol derivatives as direct dyeing nitro dyes.

Nitro dyes have attained a substantial importance for hair dyeing. Hair dye compositions which are capable of dyeing in natural or fashionable shades without the addition of oxidizing agents can be produced by means of combining different nitro dyes. The nitro dyes are also important components of oxidizing hair dye compositions in which they are utilized for rounding off the dyeing results and for producing fashionable effects.

Such nitro dyes which can impart an intensive red coloring to the hair are required in particular for producing fashionable red effects.

For a long time, 2-nitro-p-phenylenediamine was used for this purpose, but it has been objected to recently on toxicological grounds.

A whole series of demands have been made on dyes to be used for dyeing human hair. They must be unobjectionable in both toxicological and dermatological respects.

Moreover, a good fastness to light, acid and friction is required for the hair dye. Its use in oxidizing hair dye compositions further requires that the nitro dyes be stable against hydrogen peroxide in ammoniacal solution and against antioxidants.

A nitro dye which is suitable as an addition to oxidative hair dye compositions must also dye the hair root with sufficient intensity, the latter being less damaged compared to the hair tips. Meeting this demand is very important for achieving a balanced dyeing result, e.g. in the coupler-developer substance combinations of 4-aminophenol and 2,4-diaminoanisole or 4-amino-3-methylphenol and 2,4-diaminoanisole which are usually frequently used. In a dye test, the more damaged hair tips are dyed a deeper red than the less damaged hair roots with such a combination. In order to balance this dyeing behavior, nitro dyes which preferably dye the hair root must be added to the hair dye compositions.

An example of such a nitro dye is 2-nitro-1,4-diaminobenzene. The dye colors the hair an intense neutral red. But it has the disadvantage that it is not favorably stable in storage, particularly in the presence of reducing agents such as ascorbic acid. Moreover, 2-nitro-1,4-diaminobenzene is mutagenic.

SUMMARY OF THE INVENTION

Therefore, it is an object of the present invention to provide a direct dyeing hair dye which is capable of dyeing the hair an intense, pure red shade and which can be better tolerated in physiological respects and is also more advantageous with respect to coloring than the hair dyes known from the prior art.

According to our invention this object is attained in an outstanding manner by a 2-amino-6-chloro-4-nitrophenol derivative of the general formula (I)

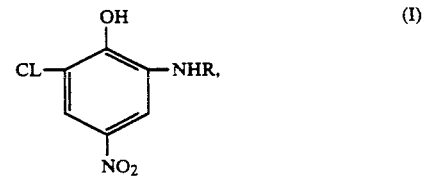

wherein the radical R designates a straight-chain or branched alkyl group with 1 to 5 carbon atoms.

Examples of the compounds of formula (I), according to the invention, are 2-chloro-6-methylamino-4-nitrophenol, 2-chloro-6-ethylamino-4-nitrophenol, 2-chloro-4-nitro-6-propylaminophenol, 2-chloro-6-((2'-methylpropyl)amino)-4-nitrophenol and 2-chloro-6-((2',2'-dimethylpropyl)amino)-4-nitrophenol.

The new nitro dyes according to the general formula (I) can be produced e.g. by means of the following processes:

According to a first process, 2-amino-6-chloro-4-nitrophenol is first reacted with a carboxylic acid chloride of the formula $R^1C(O)Cl$ or a carboxylic acid anhydride of the formula $O(C(O)R^1)_2$, wherein $R^1$ is hydrogen or a straight-chain or branched alkyl group with 1 to 4 carbon atoms, and the resulting $R^1$-substituted N-(3-chloro-2-hydroxy-5-nitrophenyl)carboxylic acid amide is then reduced with sodium borohydride in the presence of boron trifluoride etherate to form the compound of formula (I). The reduction step is preferably carried out at 60 degrees Celsius in tetrahydrofuran as solvent.

According to a second process, 2-amino-6-chloro-4-nitrophenol is first dissolved in a carboxylic acid of the formula $R^1C(O)OH$, wherein $R^1$ is hydrogen or a straight-chain or branched alkyl group with 1 to 4 carbon atoms, the solution thus obtained is then mixed with sodium borohydride and the reaction mixture is subsequently heated to 60 to 70 degrees Celsius. The desired alkylation product can be isolated very simply by means of diluting the reaction mixture with water.

According to a third process, 2-amino-6-chloro-4-nitrophenol is first reacted with an orthocarboxylic acid ester of the formula $R^1C(OR^2)_3$, wherein $R^1$ is hydrogen or a straight-chain or branched alkyl group with 1 to 4 carbon atoms and $R^2$ is methyl or ethyl, and the obtained benzoxazole derivative is then reduced with sodium borohydride in alcoholic solution.

E.g. triethyl orthoformate, trimethyl orthoformate and triethyl orthoacetate are taken into consideration as suitable orthocarboxylic acid esters.

The new nitro dyes of formula (I) comprise advantageous surprising characteristics.

According to the prior art, the shade of an aminonitrophenol can be shifted toward red in that this aminonitrophenol is substituted in amino nitrogen with a hydroxy-alkyl group. However, it has been found that the substitutions of the amino group in the 2-amino-6-chloro-4-nitrophenol with a 2-hydroxyethyl group causes only a minimal shifting of color. On the other hand, it has been found in a surprising manner that dyes capable of dyeing hair in deep, intensive red shades are obtained when substituting the amino group in 2-amino-6-chloro-4-nitrophenol with an alkyl group.

Moreover, the compounds of formula (I) have better physiological characteristics than known red-dyeing nitro dyes of the prior art. Thus, e.g. the compound 2-chloro-6-ethylamino-4-nitrophenol shows no mutagenicity in an Ames mutagenicity test with the Salmonella typhimurium strain TA 98, whereas 2-nitro-1,4-diaminobenzene is mutagenic.

The new compounds of formula (I) also possess surprising technical advantages with respect to application. The hair dye specialist expects that the intensity of the achievable hair coloring is decreased when a dye molecule is increased and when the solubility in water is reduced. But, surprisingly, it has been found that, although the solubility in water decreases in the substitution of the basic body 2-amino-6-chloro-4-nitrophenol in the amino group as the magnitude of the substituents decreases, the intensity of the achieved hair coloring does not decrease.

In addition, it has been found in dye tests with the dyes according to the invention, e.g. 2-chloro-6-((2'-methylpropyl)amino-4-nitrophenol, that the hair root is dyed a lustrous red shade. Such a dyeing result was obtained previously only with 2-nitro-p-phenylenediamine. The new compounds according to the general formula (I) therefore constitute a substantial advance in hair dye technology, since it is now possible to replace the 2-nitro-p-phenylenediamine, which was objectionable on toxicological grounds, with a compound which is technically equivalent but improved in toxicological respects.

Antioxidants such as ascorbic acid or sodium sulfite must be added to oxidative hair dye compositions which, as dye precursors, contain e.g. a combination of p-phenylenediamine, p-aminophenol or their derivatives with meta-substituted benzene derivatives such as resorcin or m-phenylenediamine derivatives, in order to prevent an unwanted darkening in color of the dye mass during production, filling and storage. Like the p-phenylenediamine or p-aminophenol derivatives used in oxidative hair dye compositions, these antioxidants are reducing agents capable of reducing certain nitro compounds.

Thus, every hair dye specialist knows that the 2-nitro-p-phenylenediamine breaks down slowly in oxidative hair dye compositions. The color shade obtained with such a hair dye composition is clearly shifted after a storage period of 3-6 months compared with a new preparation. Surprisingly, this unwanted behavior can be prevented if the new compounds according to the general formula (I) are used as red component instead of the 2-nitro-p-phenylenediamine. The storage stability of a hair dye composition containing the new red nitro dyes is clearly improved compared to the conventional formulations corresponding to the prior art.

The nitro-p-phenylenediamine can be replaced in the hair dye compositions by the compound of formula (I) in full measure and in an advantageous manner.

The subject matter of the present application is therefore also a composition for dyeing hair containing dye and cosmetic additives for hair dye compositions, characterized in that it contains 2-amino-6-chloro-4-nitrophenol derivatives of the general formula (I)

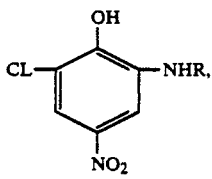

wherein the radical R is a straight-chain or branched alkyl group with 1 to 5 carbon atoms or its physiologically tolerated water-soluble salt.

The composition for dyeing hair, according to the invention, is directed to an embodiment form in which it is used without the addition of an oxidizing agent as well as to another embodiment form in which the addition of an oxidizing agent is required.

The first hair dye composition without the addition of an oxidizing agent is a composition which can contain other known direct dyeing hair dyes in addition to the dyes of the indicated formula (I). Of these dyes known for dyeing hair, the following are mentioned by way of example: aromatic nitro dyes such as 2-amino-4-nitrophenol, 1-(2'-hydroxyethyl)amino-2-amino-4-nitrobenzene, 2-nitro-4-(2'-hydroxyethyl)aminoaniline, 1-methylamino-2-nitro-4-di-(2'-hydroxyethyl)aminobenzene, 1-(2',3'-dihydroxypropyl)-amino-2-nitro-4-(N-ethyl,N-(2''-hydroxyethyl)amino)benzene, 1-(2',3'-dihydroxypropyl)amino-2-nitro-4-dimethylaminobenzene, 1-(2',3'-dihydroxypropyl)amino-2-nitro-4-pyrrolidinobenzene, 1-(3'-hydroxypropyl)amino-2-nitro-4-di-(2''-hydroxyethyl)-aminobenzene, 2,5-bis(2'-hydroxyethyl)aminonitrobenzene, triphenylmethane dyes such as Basic Violet 1 (C.I. 42535), azo dyes such as Acid Brown 4 (C.I. 14805), Disperse Violet 4 (C.I. 61105), anthraquinone dyes such as 1,4,5,8-tetraaminoanthraquinone or 1,4-diaminoanthraquinone, wherein the dyes of these classes can have an acidic, nonionogenic or basic character depending on their substituents. Other suitable dyes directly absorbed in the hair are described e.g. in the book by J. C. Johnson, "Hair Dyes", Noyes Data Corp., Park Ridge (U.S.A.) (1973), pages 3 to 91 and 113 to 139.

The preparation form of the hair dye composition based on direct dyeing dyestuffs described here can be e.g. a solution, particularly an aqueous-alcoholic solution. Preferred preparation forms are cream, gel or emulsion. It is likewise possible to dispense this composition from a pressurized container as aerosol spray or aerosol foam by means of an atomizer or other suitable pump or spray devices or in combination with conventional propellants liquified under pressure.

The dyes of the indicated formula (I) are contained in these dye compositions without the addition of oxidizing agents in a concentration of approximately 0.01 to 2.0 percent by weight, preferably 0.01 to 1.0 percent by weight. The total contents of direct dyeing dyestuffs lies within the boundaries of approximately 0.01 to 3.0 percent by weight.

The pH value of this dye composition is in the range of 3 to 12, particularly at pH 8 to 11.5, wherein the desired alkaline pH value is preferably adjusted with ammonia, but can also be effected with organic amines such as monoethanolamine or triethanolamine.

The application of this dye composition is effected in the usual manner by means of applying to the hair a sufficient quantity of the composition for dyeing the hair, the composition remains in contact with the hair for a period of approximately 5 to 10 minutes. The hair is subsequently rinsed with water, possibly also with an aqueous solution of a weak organic acid, and dried. E.g. acetic acid, citric acid or tartaric acid can be used as weak organic acid.

Of course, the hair dye composition without the addition of oxidizing agents described above can also contain synthetic, natural or modified natural polymers conventionally used in cosmetics, so that a fixing of the hair is achieved simultaneously with the dyeing. Such compositions are designated in general as shade fixatives or color fixatives.

Of the synthetic polymers known for this purpose in cosmetics, the following are mentioned by way of example: polyvinylpyrrolidone, polyvinyl acetate, polyvinyl alcohol or polyacrylic compounds such as polyacrylic acid or polymethacrylic acid, basic polymerizates of esters of polyacrylic acid, polymethacrylic acid and amino alcohols or their salts or quaternization products, polyacrylonitrile, polyvinyl acetates and copolymerizates of such compounds as polyvinylpyrrolidone vinyl acetate and the like.

Natural polymers or modified natural polymers such as chitosan (deacetylated-chitin) or chitosan derivatives can also be used for the aforementioned purpose.

The cosmetic polymers are contained in this composition in the usual amount for such compositions, approximately 1 to 5 percent by weight. The pH value of the composition is in the range of approximately 6.0 to 9.0.

The use of this hair dye composition with additional fixing is effected in a known and conventional manner by means of moistening the hair with the fixative, fixing (setting) the hair for styling, and subsequent drying.

Of course, the hair dye composition without addition of oxidizing agents described above can also possibly contain other conventional additions for hair dye compositions, such as grooming materials, wetting agents, thickeners, emollients, preservatives and perfume oils as well as other conventional additions listed in the following for oxidizing hair dye compositions.

As mentioned in the beginning, the subject matter of the present invention also includes a hair dye composition in which the addition of an oxidizing agent is required. In addition to the dyestuffs according to the indicated formula (I) and possibly known dyestuffs which are absorbed directly in the hair, it contains additional known oxidation dyes which require an oxidative development.

These oxidation dyes are chiefly aromatic p-diamines and p-aminophenols such as p-toluylene diamine, p-phenylenediamine, p-aminophenol and similar compounds which are combined for the purpose of tinting the color with so-called modifiers such as m-phenylenediamine, resorcin, m-aminophenol and others.

Such oxidation dyes which are conventional and known for dyeing hair are described, among others, in the book by E. Sagarin, "Cosmetics, Science and Technology" (1957), Interscience Publishers Inc., New York, pages 503 ff. and in the book by H. Janistyn, "Handbook of Cosmetics and Fragrances" (1973), pages 338 ff.

Natural blond and brown shades as well as fashionable tints can be very favorably produced with mixtures of these oxidation dyes and the dyes according to the indicated formula (I).

The dyes according to formula (I) are contained in this dye composition with the addition of oxidizing agents in a concentration of approximately 0.01 to 4.0 percent by weight, preferably 0.02 to 2.0 percent by weight. The total content of dyestuffs in this dye composition is approximately 0.1 to 5.0 percent by weight.

Oxidizing hair dye compositions are generally alkaline, preferably adjusted to a pH value of approximately 8.0 to 11.5, wherein the adjustment is chiefly effected with ammonia. However, other organic amines can also be used, e.g. monoethanolamine or triethanolamine.

Hydrogen peroxide and its addition compounds are primarily considered as oxidizing agents for developing the hair coloring. The preparation form of this hair dye composition can be the same as for the hair dye composition without the addition of oxidizing agents. It is preferably a cream or a gel.

Standard cosmetic additives in creams, emulsions or gels are e.g. solvents such as water, lower aliphatic alcohols, e.g. ethanol, propanol, isopropanol, glycerin or glycols such as ethylene glycol and propylene glycol, and wetting agents or emulsifiers from the classes of anionic, cationic, amphoteric or nonionogenic surface-active substances such as e.g. fatty alcohol sulfates, fatty alcohol ether sulfates, alkyl sulfonates, alkyl benzene sulfates, alkyltrimethylammonium salts, alkyl betaines, ethoxylated fatty alcohols, ethoxylated nonylphenols, fatty acid alkanol amides, ethoxylated fatty acid esters, and thickeners such as higher fatty alcohols, bentonite, starch, polyacrylic acid, and cellulose derivatives such as carboxymethyl cellulose, alginates, vaseline, paraffin oil and fatty acids, as well as grooming materials such as lanolin derivatives, cholesterin, pantothenic acid and betaine, and perfume oils and complexing agents. The aforementioned components are used in quantities which are conventional for such purposes, e.g. the wetting agents and emulsifiers can be contained in concentrations of approximately 0.5 to 30 percent by weight, while the thickeners can be contained in a quantity of approximately 0.1 to 5 percent by weight in the preparations.

The aforementioned preparation in which the addition of an oxidizing agent is required is applied in a known manner in that the hair dye composition is mixed with the oxidizing agent before treatment and a quantity of the mixture sufficient for dyeing the hair, generally approximately 50 to 150 ml, is applied to the hair. After allowing the composition to act for a sufficient period of time, which is usually approximately 10 to 45 minutes, the hair is rinsed with water, possibly subsequently with the aqueous solution of a weak organic acid, e.g. citric acid or tartaric acid, and then dried.

Depending on the type and composition of the dye components, the hair dye composition according to the invention offers a wide range of different color shades ranging from natural color shades to highly fashionable lustrous shades. The dye composition is applied either in connection with hydrogen peroxide or also without oxidizing agents, depending on the composition.

The following examples will explain the subject matter of the Application without limiting it to the examples.

PRODUCTION EXAMPLES

Example 1

Production of 2-chloro-6-ethylamino-4-nitrophenol

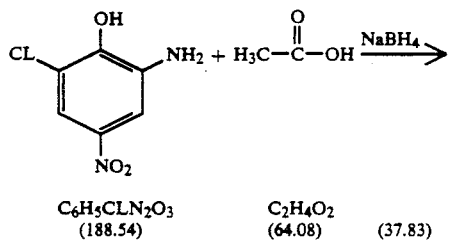

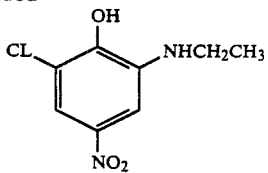

C₈H₉CLN₂O₃
(216.6)

3.77 g (20 mmoles) of 2-amino-6-chloro-4-nitrophenol are dissolved in 100 ml acetic acid. 3.03 g (80 mmoles) of sodium borohydride are then added at 10 degrees Celsius. The mixture is stirred for an hour at room temperature and then heated for three hours to 60 degrees Celsius. The mixture is diluted with 200 ml water and adjusted to a pH value of 5 with 30 percent sodium hydroxide solution for preparation. The precipitated product is removed by suction, washed with water and dried over calcium chloride in the desiccator. 2.0 g (47 percent theoretical) of orange-brown crystals are obtained which melt between 134 and 137 degrees Celsius.

The reaction described in Example 1 can also be carried out with homologous carboxylic acids. When isobutyric acid is used a product is obtained which is identical to Example 5, Stage 2 and when using pivalic acid a product is obtained which is identical to Example 6, Stage 2.

Example 2

Production of 2-chloro-6-ethylamino-4-nitrophenol

1st Stage:
N-(3-chloro-2-hydroxy-5-nitrophenyl)acetamide

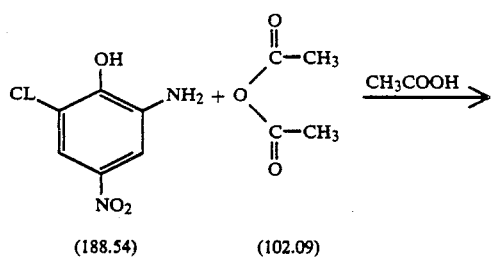

(188.54)    (102.09)

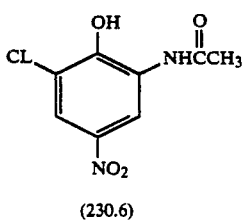

(230.6)

70 g (0.37 mmoles) of 2-amino-6-chloro-4-nitrophenol are placed in 500 ml acetic acid in a flask. 100 ml (1.06 mol) of acetic acid anhydride are added by drops at 25 degrees Celsius accompanied by stirring. The mixture is stirred for 5 hours at room temperature. The mixture is then poured on 2.5 kg ice water and stirred for another hour. The precipitated product is removed by suction, washed with water and recrystallized from 2 parts ethanol and one part water. 59.9 g (69.9 percent theoretical) of beige powder with a melting point above 200 degrees Celsius is obtained.

2nd Stage:
2-chloro-6-ethylamino-4-nitrophenol

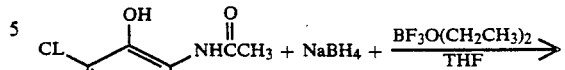

(230.6)    (37.8)    (141.93)

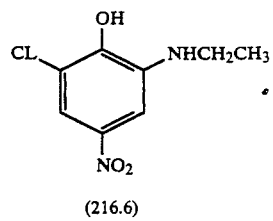

(216.6)

50 g (0.22 mols) of N-(3-chloro-2-hydroxy-5-nitrophenyl)-acetamide from Stage 1 is placed in 600 ml dried tetrahydrofuran in a nitrogen atmosphere. 18.9 g (0.5 moles) of sodium borohydride are then added accompanied by cooling. When the hydrogen development has subsided, 85 ml (0.68 moles) of boron trifluoride ethyl etherate is added by drops accompanied by cooling. The reaction is exothermic and is maintained at 30 degrees Celsius by means of cooling. After ending the addition, the mixture is heated for 2 hours to 60 degrees Celsius. The mixture is subsequently hydrolyzed at 0 degrees Celsius with 185 ml of a mixture of tetrahydrofuran and water (ratio 1:1), acidified with 110 ml semi-concentrated hydrochloric acid and stirred for an hour at room temperature. The product is isolated by extraction with 23×250 ml diethyl ether after the reaction mixture has been adjusted to a pH value of 5 with sodium hydroxide solution. The ether phase is washed with saturated sodium chloride solution and dried over magnesium sulfate. The raw product is recrystallized from ethanol and water (2:1). 40.6 g (86.5 percent theoretical) of brown to dark-brown needles are obtained which have a melting point between 136 and 138 degrees Celsius.

| CHN Analysis: | % C | % H | % N |
| --- | --- | --- | --- |
| C₈H₉ClN₂O₃ | | | |
| calculated: | 44.36 | 4.19 | 12.93 |
| found: | 44.33 | 4.25 | 12.93 |

The product which has been produced in this way is identical to the product which was described in Example 1.

Example 3

Production of 2-chloro-6-((2-hydroxyethyl)amino)-4-nitrophenol

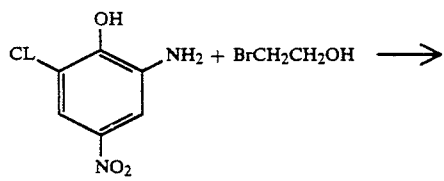

C₆H₅ClN₂O₃      C₂H₅BrO
(188.54)          (124.97)

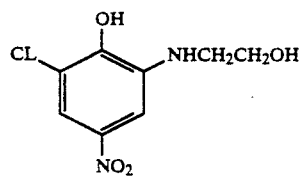

C₈H₉ClN₂O₄
(232.6)

1.88 g (10 mmoles) of 2-amino-6-chloro-4-nitrophenol, 40 ml of 2-bromoethanol and 1.0 g (10 mmoles) of calcium carbonate are heated for an hour to 120 degrees Celsius. The mixture is then diluted with 300 ml water and adjusted to a pH value of 12 with sodium hydroxide solution. The aqueous phase is extracted with 3×40 ml diethyl ether. The extract contains secondary products and is disposed of. The aqueous phase is adjusted to a pH value of 5 with hydrochloric acid and extracted with 5×50 ml diethyl ether. The ether phase is dried over magnesium sulfate. The residue obtained after distilling off the solvent is recrystallized twice from water. 0.68 g (29 percent theoretical) of orange-colored powder are obtained which melts between 142 and 144 degrees Celsius.

| CHN Analysis: | % C | % H | % N |
|---|---|---|---|
| C₈H₉ClN₂O₄ × ½ H₂O | | | |
| calculated: | 39.75 | 4.14 | 11.59 |
| found: | 40.15 | 4.16 | 11.61 |

Example 4

Production of 2-chloro-4-nitro-6-propylaminophenol

1st Stage:
N-(3-chloro-2-hydroxy-5-nitrophenyl)propionic acid amide

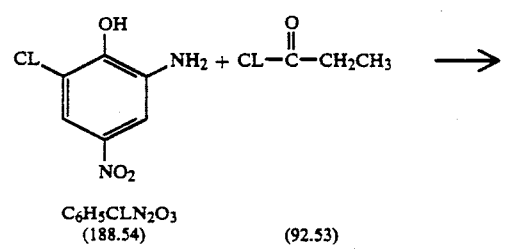

C₆H₅ClN₂O₃
(188.54)          (92.53)

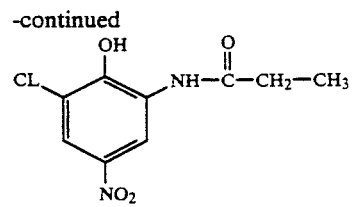

C₉H₉ClN₂O₄
(244.64)

9.43 g 50 mmoles) of 2-amino-6-chloro-4-nitrophenol is dissolved in 200 ml dioxane in a three-neck flask with reflux condenser, thermometer and drip funnel accompanied by stirring. 6.20 g (5.85 ml; 67 mmoles) of propionic acid chloride are then added by drops at room temperature. The mixture is stirred for two hours at room temperature and then heated for one hour to 90 degrees Celsius. The mixture is then poured on 500 g ice. The precipitated, beige precipitate is removed by suction and recrystallized from a mixture of ethanol and water (1:1).

9.21g (75 percent theoretical) of a brown-beige product are obtained which melts at 167 degrees Celsius accompanied by decomposition.

| CHN Analysis: | % C | % H | % N |
|---|---|---|---|
| C₉H₉ClN₂O₄ | | | |
| calculated: | 44.19 | 3.71 | 11.45 |
| found: | 44.24 | 3.77 | 11.30 |

2nd Stage:
2-chloro-4-nitro-6-propylaminophenol

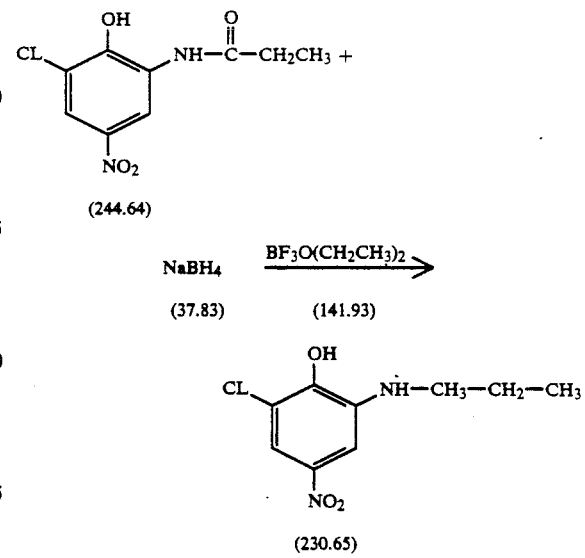

7.34 g (30 mmoles) of N-(3-chloro-2-hydroxy-5-nitrophenyl)-propionic acid amide from Stage 1 are placed in 100 ml dried tetrahydrofuran in a nitrogen atmosphere. 2.27 g (60 mmoles) of sodium borohydride are now added accompanied by cooling. When the hydrogen development has subsided, 11.3 ml (90 mmoles) of boron trifluoride ethyl etherate is added by drops accompanied by cooling. The reaction is exothermic and is maintained at 30 degrees Celsius by means of cooling. The reaction mixture is then heated for 2 hours to 60 degrees Celsius. The mixture is subsequently cooled to 0 degrees Celsius and hydrolyzed with 15 ml of a mixture of tetrahydrofuran and water (ratio 1:1), acidified with 10 ml semi-concentrated hydrochloric acid and stirred for an hour at room temperature. The product is isolated by extraction with 3×100 ml diethyl ether after being adjusted to a pH value of 5 with sodium hydroxide solution. The ether phase is washed with saturated sodium chloride solution and dried over magnesium sulfate. The raw product is recrystallized from 200 ml cyclohexane. 4.00 g (58.5 percent theoretical) of a yellow-orange powder are obtained which has a melting point between 81 and 82.5 degrees Celsius.

| CHN Analysis: | % C | % H | % N |
|---|---|---|---|
| C9H11ClN2O3 | | | |
| calculated: | 46.87 | 4.81 | 12.15 |
| found: | 46.52 | 4.93 | 11.85 |

Example 5

Production of
2-chloro-6-((2-methylpropyl)amino-4-nitrophenol)

1st Stage:
N-(3-chloro-2-hydroxy-5-nitrophenyl)isobutyric acid amide

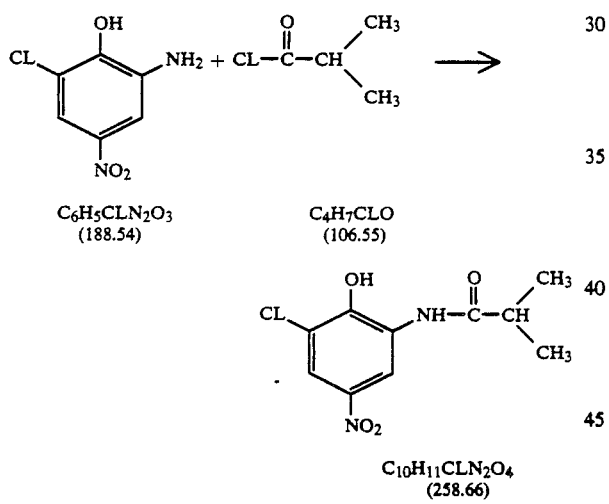

Composition

| 9.43 g | (50 mmoles) | 2-amino-6-chloro-4-nitrophenol |
| 150 ml | | tetrahydrofuran |
| 7.14 g | (67 mmoles) | isobutyric acid chloride |

The compound is produced in a manner analogous to that described in Example 4, Stage 1.

10.1 g (75 percent theoretical) of a beige product are obtained which melts at 158 degrees Celsius accompanied by decomposition.

| CHN Analysis: | % C | % H | % N |
|---|---|---|---|
| C10H11ClN2O4 | | | |
| calculated: | 46.44 | 4.29 | 10.93 |
| found: | 46.46 | 4.38 | 10.59 |

2nd Stage:
2-chloro-6-((2'-methylpropyl)amino-4-nitrophenol

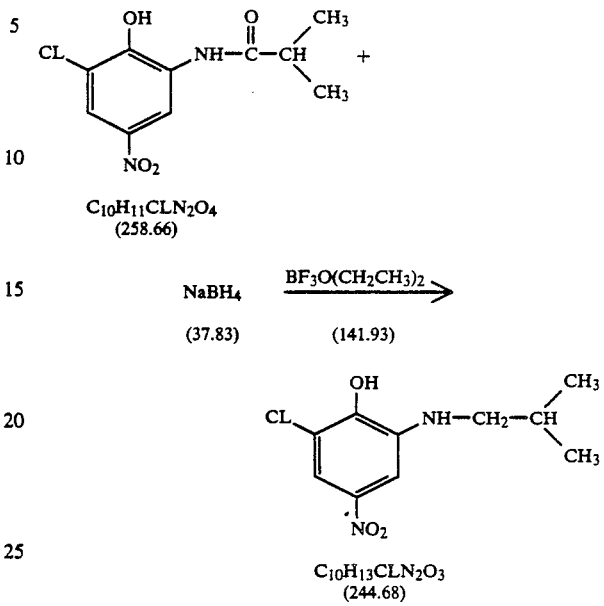

Composition

| 7.76 g | (30 mmoles) | N-(3-chloro-2-hydroxy-5-nitrophenyl) isobutyric acid amide from Stage 1 |
| 100 ml | | tetrahydrofuran |
| 2.27 g | (60 mmoles) | sodium borohydride |
| 11.3 ml | (90 mmoles) | boron trifluoride-diethyl etherate |

The compound is produced in a manner analogous to that described in Example 4, Stage 2. 6.0 g (82 percent theoretical) of an orange product are obtained which melts between 115 and 116 degrees Celsius.

| CHN Analysis: | % C | % H | % N |
|---|---|---|---|
| C10H13ClN2O3 | | | |
| calculated: | 49.09 | 5.36 | 11.45 |
| found: | 48.90 | 5.45 | 11.27 |

Example 6

Production of
2-chloro-6-((2',2'-dimethylpropyl)amino-4-nitrophenol)

1st Stage:
N-(3-chloro-2-hydroxy-5-nitrophenyl)pivalic acid amide

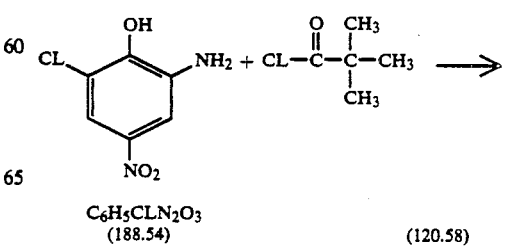

-continued

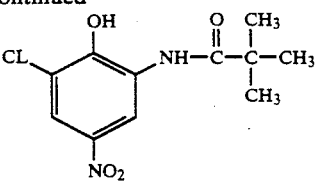

C₁₁H₁₃ClN₂O₄
(272.7)

Composition

| | | | |
|---|---|---|---|
| 9.43 g | | (50 mmoles) | 2-amino-6-chloro-4-nitrophenol |
| 150 ml | | | tetrahydrofuran |
| 6.63 g | (6.77 ml) | (55 mmoles) | pivalic acid chloride |

The compound is produced in a manner analogous to that described in Example 4, Stage 1. 10.7 g (78 percent theoretical) of a beige powder are obtained which melts at 140 degrees Celsius accompanied by decomposition.

2nd Stage:
2-chloro-6-((2',2'-dimethylpropyl)amino)-4-nitrophenol)

Reaction

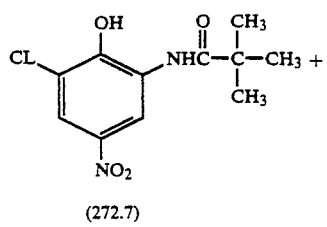

(272.7)

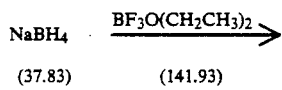

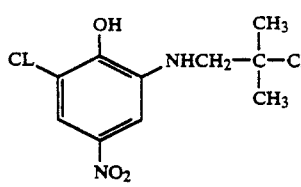

C₁₁H₁₅ClN₂O₃
(258.7)

Composition

| | | | |
|---|---|---|---|
| 25 g | | (91.7 mmoles) | N-(3-chloro-2-hydroxy-5-nitrophenyl) pivalic acid amide from Stage 1 |
| 7.99 g | | (211 mmoles) | sodium borohydride |
| 260 ml | | | tetrahydrofuran |
| 40.68 g | (36 ml) | (286 mmoles) | boron trifluoride-diethyl etherate |

The compound is produced in a manner analogous to that described in Example 4, Stage 2. After crystallization from a mixture of ethanol and water (1:1), 19.3 g (81 percent theoretical) of a reddish-brown powder are obtained which melts between 110 and 111 degrees Celsius.

| CHN Analysis: | % C | % H | % N |
|---|---|---|---|
| C₁₁H₁₅ClN₂O₃ | | | |
| calculated: | 51.07 | 5.84 | 10.83 |
| found: | 51.10 | 5.89 | 10.73 |

Example 7

Production of 2-chloro-6-methylamino-4-nitrophenol

1st Stage:
7-chloro-5-nitrobenzoxazole

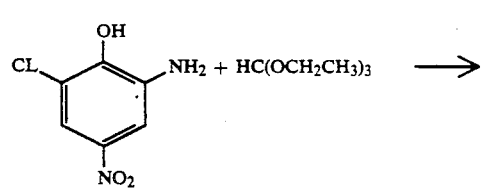

C₆H₅ClN₂O₃        C₇H₁₆O₃
(188.54)          (148.20)

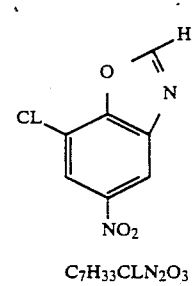

C₇H₃₃ClN₂O₃
(148.20)

3.77 g (20 mmoles) of 2-amino-6-chloro-4-nitrophenol and 41.0 g (46 ml; 277 mmoles) of triethyl orthoformate are heated for three hours under reflux (oil bath temperature 120 to 130 degrees Celsius). The orthoformate which is not reacted is then distilled off at 149 degrees Celsius and the residue is absorbed in 50 ml warm ethanol. When cooled off to 0 degrees Celsius, the product is crystallized out. It is removed by suction, washed with warmer ethanol and dried. 2.7 g (68 percent theoretical) of yellow-beige crystals are obtained which melt between 120 and 122.5 degrees Celsius.

| CHN Analysis: | % C | % H | % N |
|---|---|---|---|
| C₇H₃ClN₂O₃ | | | |
| calculated: | 42.34 | 1.52 | 14.11 |
| found: | 42.19 | 1.66 | 14.02 |

2nd Stage:
2-chloro-6-methylamino-4-nitrophenol

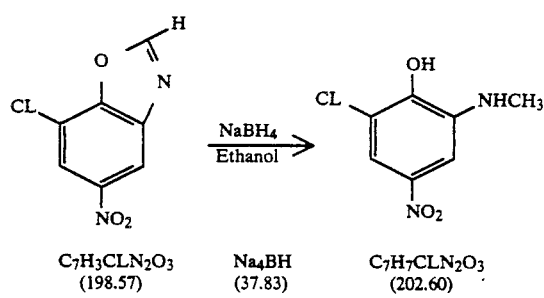

| C7H3ClN2O3 | Na4BH | C7H7ClN2O3 |
| (198.57) | (37.83) | (202.60) |

2.0 g (10 mmoles) of the product obtained in Stage 1 are suspended in ethanol at 0 degrees Celsius and gradually mixed with 2.0 g (53 mmoles) of sodium borohydride. The mixture heats up and turns red. It is stirred for 30 minutes at room temperature. The mixture is then filtrated and the ethanol is distilled off. The residue is mixed with 200 g water. The red solution is adjusted to a pH value of four with double-strength hydrochloric acid. The precipitated beige product is sucked off and recrystallized from water. 2.0 g (50 percent theoretical) of a yellow crystalline substance are obtained which melts between 147 and 149 degrees Celsius.

| CHN Analysis: | % C | % H | % N | % Cl |
|---|---|---|---|---|
| C7H7ClN2O3 | | | | |
| calculated: | 41.50 | 3.48 | 13.83 | 17.50 |
| found: | 41.36 | 3.67 | 13.78 | 17.43 |

EXAMPLE FOR HAIR DYE COMPOSITION

Examples 8–13: Hair Dye Composition 2-amino-6-chloro-4-nitrophenol, 6-chloro-2-((2'-hydroxyethyl)-amino)-4-nitrophenol or the dyes of formula (I), wherein R=CH3, C2H5, CH2—CH(CH3)2 or CH2—C(CH3)3, were added to a hair dye solution of the following composition:

| 0.3 g | dyestuff |
| 2.0 g | lauryl alcohol diglycol ether sulfate sodium salt (28 percent aqueous solution) |
| 2.0 g | ammonia (25 percent aqueous solution) |
| 95.7 g | water |
| 100.0 g. | |

Bleached human natural hair was treated for 20 minutes at room temperature with a solution according to Example 8–13. The hair is then rinsed with water and dried. The hair is dyed as indicated in Table 1:

TABLE 1

| Example | Dyestuff | Hair color |
|---|---|---|
| 8 | 2-amino-6-chloro-4-nitrophenol | orange |
| 9 | 6-chloro-2-((2'-hydroxyethyl)amino)-4-nitrophenol | orange |
| 10 | compound of formula (I) (R = CH3) | red |
| 11 | compound of formula (I) (R = C2H5) | red |
| 12 | compound of formula (I) (R = CH2—CH(CH3)2) | lustrous red |
| 13 | compound of formula (I) (R = CH2—C(CH3)3) | lustrous red |

Example 14: Hair Dye Solution With Setting Action

| 0.1 g | 2-chloro-6-ethylamino-4-nitrophenol |
| 2.0 g | polyvinylpyrrolidone |
| 0.1 g | glycerin |
| 40.0 g | isopropanol |
| 57.8 g | water |
| 100.0 g | |

White human hair is set for styling with the color fixing solution and dried. The hair is dyed red and fixed.

Example 15: Oxidizing Hair Dye Composition

| 0.40 g | 2,5-diaminotoluene sulfate |
| 0.26 g | resorcin |
| 0.40 g | 4-aminophenol |
| 0.13 g | 2,4-diaminoanisole |
| 0.50 g | dyestuff according to Example 2 |
| 0.30 g | ethylenediaminetetraacetic acid disodium salt |
| 0.30 g | ascorbic acid |
| 15.00 g | cetyl alcohol |
| 3.50 g | lauryl alcohol diglycol ether sulfate sodium salt (28 percent aqueous solution) |
| 6.00 g | ammonia, (25 percent aqueous solution) |
| 73.21 g | water, de-ionized |
| 100.00 g | |

50 ml of the above hair dye composition are mixed shortly before application with 50 ml hydrogen peroxide solution (6 percent). The mixture is then applied to gray human hair and allowed to act for 30 minutes at a temperature of 40 degrees Celsius. After rinsing the hair with water and subsequent drying, the hair has a rosewood shade. The hair is dyed uniformly from the root to the tips of the hair.

While the invention has been illustrated and described as embodied in 2-amino-6-chloro-4-nitrophenol derivatives, process for their production and hair dyes containing those compounds, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

We claim:

1. 2-amino-6-chloro-4-nitrophenol derivative of the general formula (I)

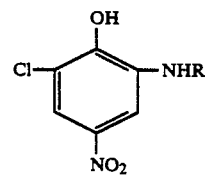

wherein the radical R is selected from the group consisting of straight-chain alkyl groups with 1 to 5 carbon atoms and branched alkyl groups with 1 to 5 carbon atoms.

2. The derivative according to claim 1, wherein said radical R is methyl.

3. The derivative according to claim 1, wherein said radical R is ethyl.

4. The derivative according to claim 1, wherein said radical R is propyl.

5. The derivative according to claim 1, wherein said radical R is 2'-methylpropyl.

6. The derivative according to claim 1, wherein said radical R is 2',2'-dimethylpropyl.

7. Composition for dyeing hair containing dye and cosmetic additives containing a member selected from the group consisting of said 2-amino-6-chloro-4-nitrophenol derivatives according to claim 1 and water-soluble salts thereof.

8. Composition according to claim 7, further comprising at least one direct dyeing hair dye.

9. Composition according to claim 8, wherein the direct dyeing hair dye is selected from 2-amino-4-nitrophenol, 1-(2'-hydroxyethyl)amino-2-amino-4-nitrobenzene, 2-nitro-4-(2'-hydroxyethyl)amino-aniline, 1-methylamino-2-nitro-4-di-(2'-hydroxyethyl)-aminobenzene, 1-(2',3'-dihydroxypropyl)-amino-2-nitro-4-(N-ethyl,N-(2''-hydroxyethyl)amino)benzene, 1-(2',3'-dihydroxy-propyl)amino-2-nitro-4-dimethylaminobenzene, 1-(2',3'-dihydroxypropyl)amino-2-nitro-4-pyrrolidinobenzene, 1-(3'-hydroxypropyl)amino-2-nitro-4-di-(2''-hydroxyethyl)-aminobenzene, 2,5-bis(2'-hydroxyethyl)aminonitrobenzene, Basic Violet 1 (C.I. 42535), Acid Brown 4 (C.I. 14805), Disperse Violet 4 (C.I. 61105), 1,4,5,8-tetraaminoanthraquinone and 1,4-diaminoanthraquinone.

10. Composition according to claim 8, further comprising at least one polymer selected from the group consisting of synthetic, natural and modified natural polymers.

11. Composition according to claim 10, wherein the polymer is selected from the group consisting of polyvinylpyrrolidone, polyvinyl acetate, polyvinyl alcohol, polyacrylic acid, polymethacrylic acid, basic polymerizates of esters of polyacrtylic acid and polymethacrylic acid and amino alcohols and their salts and quaternization products, polyacrylonitrile, polyvinyl acetate, polyvinylpyrrolidone vinyl acetate and chitosan and chitosan derivatives.

12. Composition according to claim 9, wherein the 2-amino-6-chloro-4-nitrophenol derivative of formula (I) is contained in a quantity of 0.01 to 2.0 percent by weight.

13. Composition according to claim 10, further comprising at least one oxidizing hair dye.

14. Composition according to claim 13, wherein the oxidizing hair dye is selected from the group consisting of phenylenediamine, p-toluylene diamine, p-aminophenol, m-phenylenediamine, resorcin and m-aminophenol.

15. Composition according to claim 13, wherein the 2-amino-6-chloro-4-nitrophenol derivative of formula (I) is contained in a quantity of 0.01 to 4.0 percent by weight.

16. Composition according to claim 11, wherein the 2-amino-6-chloro-4-nitrophenol derivative of formula (I) is contained in a quantity of 0.01 to 2.0 percent by weight.

* * * * *